United States Patent
Lockwood (10) Patent No.: US 6,478,023 B1
(45) Date of Patent: Nov. 12, 2002

(54) SKIN STABILIZATION AND NASAL DILATOR SYSTEM

(76) Inventor: Hanford N. Lockwood, 2222 Alameda de las Pulgas, San Mateo, CA (US) 94403

(*) Notice: Subject to any disclaimer, the term of this patent is extended or adjusted under 35 U.S.C. 154(b) by 0 days.

(21) Appl. No.: 09/329,663

(22) Filed: Jun. 10, 1999

(51) Int. Cl.7 ................................................ A61M 15/00
(52) U.S. Cl. ........................ 128/200.24; 128/209.18; 606/204.45
(58) Field of Search ................... 128/200.24, 201.18, 128/898, 858, 209.18; 2/9, 206, 455; 606/204.45

(56) References Cited

U.S. PATENT DOCUMENTS

| | | | |
|---|---|---|---|
| 701,538 A | | 6/1902 | Carence |
| 1,256,188 A | | 2/1918 | Wilson |
| 1,292,083 A | * | 1/1919 | Sawyer |
| 1,950,839 A | | 3/1934 | Chirila |
| 2,055,855 A | | 9/1936 | Weaver |
| 2,264,153 A | | 11/1941 | Rowe |
| 2,277,390 A | | 3/1942 | Crespo |
| 2,674,245 A | | 4/1954 | Tanditter |
| 2,715,904 A | | 4/1955 | Hill |
| 3,905,335 A | | 9/1975 | Kapp |
| 3,935,859 A | | 2/1976 | Doyle |
| 4,201,217 A | | 5/1980 | Slater |
| 4,221,217 A | | 9/1980 | Amezcua |
| 4,267,831 A | | 5/1981 | Aguilar |
| 4,327,719 A | | 5/1982 | Childers |
| 4,414,977 A | | 11/1983 | Rezakhany |
| 5,476,091 A | * | 12/1995 | Johnson |
| 5,479,944 A | * | 1/1996 | Petruson |
| 5,533,499 A | * | 7/1996 | Johnson |
| 5,546,929 A | | 8/1996 | Muchin |
| 5,549,103 A | * | 8/1996 | Johnson |
| 5,553,605 A | * | 9/1996 | Muchin |
| 5,609,150 A | * | 3/1997 | Maged |
| 5,653,224 A | * | 8/1997 | Johnson |
| 5,890,486 A | * | 4/1999 | Mitra et al. |
| 5,931,854 A | * | 8/1999 | Dillon |

FOREIGN PATENT DOCUMENTS

| | | |
|---|---|---|
| ES | 289561 | 10/1985 |

* cited by examiner

Primary Examiner—Michael A. Brown
Assistant Examiner—Lalita Hamilton
(74) Attorney, Agent, or Firm—Townsend and Townsend and Crew LLP (57) ABSTRACT

A skin stabilization system is formed from lamination elements consisting of fabric layers bonded to plastic layers which in turn are laminated to the outer surface of the user's skin by adhesively attaching them thereto. The lamination elements resist tension, compression and bending forces and are used to strengthen or stabilize the skin to reduce deformation. The lamination elements can be applied as a single unit or interconnected to other lamination elements by extending the fabric portions of the laminate. The skin stabilization system can be used as a nasal dilator. As a nasal dilator, a lamination element is applied to each side of the nose between the bridge and the cheek, which in turn causes the center of the lamination element to lift the soft outer skin of the nasal passage and prevent any deflection that restricts breathing through the nasal passages. The fabric portions of the lamination element can be extended over the bridge of the nose to interconnect the two nasal dilator lamination elements and assist the user in properly positioning the elements.

9 Claims, 4 Drawing Sheets

SKIN STABILIZATION AND NASAL DILATOR SYSTEM

BACKGROUND OF THE INVENTION

This invention relates to a new field of devices which can be derived from lamination elements consisting of fabric materials bonded to layers of plastic which are resistant to tension, compression and bending forces. The lamination elements when properly applied by the user include a layer that integrates the outer surface of skin into the lamination element. The lamination element with its ability to resist these forces is used to strengthen or stabilize the skin in a way that reduces deformation and can strengthen or reinforce soft skin tissue to prevent deformation under some conditions.

One use of such a skin stabilizing lamination element is to prevent deformation of the soft tissue (as used in this application, typically referring to soft tissue, including the overlying skin) external to a nasal passage on the side of the nose. A lamination element can be applied on one side of the nose between the bridge of the nose and the cheek, which in turn causes the center of the lamination to hold the soft outer tissue of the nasal passage and prevent any deflection that restricts breathing through the respective nasal passage. A similar but opposite-shaped lamination element is required on the opposite side of the nose to stabilize the outer tissue of the second nasal passage.

Blockage of the nasal passages for reasons such as swelling due to allergies, colds, and physical deformities can lead to breathing difficulty and discomfort. The nasal passages have mucus membranes which condition the air in the nasal passages prior to its arrival in the lungs. If the nasal passages are constricted due to swelling or minor deformities, then the alternative is to breathe through the mouth. This means that the air bypasses the mucus membranes, losing the conditioning effects and causing irritation in the throat and lungs. At night, restrictions to breathing through the nasal passages can lead to snoring and/or sleep disturbances. In some cases, the restricted air supply can cause sleep problems brought on by a lack of oxygen.

For people with chronic blockages in the nasal passages, the alternative to correct the problem has been expensive surgery or medication. People with minor deformities and breathing problems brought on by swelling of the walls of the nasal passageways have been turning to various products fitted in or on the nose which claim to open the nasal passages.

The structure of the nose limits the options available for the design of nasal dilators. The nose terminates at the nostril, which has a slightly expanded volume immediately above it known as the vestibule. Above the vestibule, the nasal passage becomes restricted at a point called the nasal valve. At the nasal valve, the external wall of the nose consists of soft tissue known as the lateral wall, which will deform with air pressure changes induced within the nasal passage during the breathing cycles. Above the nasal valve, the nasal passage opens up to a cavity with turbinates over the top of the palate and turns downward to join the passage from the mouth to the throat.

The external structure of the nose consists of tissue and skin covering the nasal bones which are part of the skull. This gives the top of the nose a rigid structure at its base. Beyond the rigid nose bones, there is thin cartilage under the tissue which is attached to the septum, which in turn contributes to the outside shape of the nose. The septum forms the wall between the two nostrils and may, if it is crooked, contribute to breathing problems.

As an alternative to surgery, the structure of the nose and the prior art leave two alternatives for the design of nasal dilators. One alternative is the type of dilator that consists of a tube or structure which can be inserted into the nasal passage to hold it in the open position allowing the free passage of air. The disadvantage of this design is that the dilator structure covers up the mucus membranes which condition the air. Also dilators of this design are uncomfortable and can irritate the walls of the nasal passage.

The second alternative is a dilator design where each end that attaches to the external lateral wall of each of the nasal passages has a resilient member connecting the ends for generating an external pulling force on the lateral wall to thereby open the nasal passage. The advantage of this design over the first alternative is that the nasal passages are not disturbed by an internal insert. However, this second alternative permits only limited control over the resilient force on the lateral wall of each of the nasal passages, and the resilient members crossing over the bridge of the nose can cause discomfort.

The present invention differs from prior art systems in that it is a laminated skin stabilizer that locally stabilizes the lateral wall of the nasal passage. The lamination element adheres to the skin at the bridge of the nose at one end and to the skin adjacent to the cheekbone structure on the other end. It stabilizes the lateral wall tissue where it adheres to the soft skin external to the nasal passage. The ability of the lamination element to resist tension, compression and bending forces prevents deformation of the soft tissue of the lateral wall and promotes easier breathing.

In the prior art, there are items, such as bandages, tapes, and splints, which have some characteristics of a laminated skin stabilization system. Bandages and tapes have adhesives which stick to the skin; however, they cannot resist compression and bending loads. Splints, on the other hand, do not adhere to the skin, but have the rigid structure required to resist compression, tension, and bending loads. Splints are usually attached to the skin using tape which is independent of the splint structure itself.

The prior art that comes closest to the present invention are the nasal dilators disclosed in patents to Muchin, Johnson, and Deubek et al, which are all limited to placing resilient members over the bridge of the nose and which function very differently from the present invention.

The development of nasal dilators goes back to U.S. Pat. No. 701,538, which was filed Sep. 16, 1901, teaches a dilator that fits within the nasal passages, and functions like the above-described first alternative. Many of the devices that fit this alternative are not only used as nasal dilators, they also teach methods for filtering air or providing a platform for releasing medication which is entrained in the air passing through the device located in the nostril. U.S. Pat. No. 1,256,188 to Wilson, U.S. Pat. No. 2,055,855 to Weaver, U.S. Pat. No. 2,264,153 to Rowe, U.S. Pat. No. 2,277,390 to Crespo, U.S. Pat. No. 2,674,245 to Tanditter, U.S. Pat. No. 2,715,904 to Hill, U.S. Pat. No. 3,905,335 to Kapp, U.S. Pat. No. 3,935,859 to Doyle, U.S. Pat. No. 4,201,217 to Slater, U.S. Pat. No. 4,221,217 to Amezcua, U.S. Pat. No. 4,267,831 to Aguilar, U.S. Pat. No. 4,327,719 to Childers, U.S. Pat. No. 4,414,977 to Rezakhany, and U.S. Pat. No. 5,479,944 to Petruson are all examples of devices which either dilate, medicate or filter by inserting the device inside the nostril.

U.S. Pat. No. 5,479,944 to Petruson is of particular interest in the group, because it has tabs which insert in each nostril which are connected to a resilient member located between them which is deformed into a curved shape when the tabs are inserted in each nostril. The single resilient member curves around the end of the nose clearing the septum and provides a biasing force to the tabs forcing them against the outer wall of each nostril, thereby causing each nostril to be opened further. This design has disadvantages over the present invention, in that the tabs in contact with the sensitive surface on the inside of the nostril can cause discomfort to the user. The tabs cannot be located far up into the vestibule or even further up to the nasal valve, so that this type of nasal dilator is of limited effectiveness. Because of the location of the tabs in the nasal passages, the Petruson dilator will interfere with any attempt by the user to clear nasal congestion. Also the biasing force is fixed by the design and size of the connecting member and is not adjustable by the user.

The second alternative is the dilator design which attaches to the outside surface of the nasal lateral walls and has a resilient member for generating a pull force on the lateral walls of the nose. An example of this type of nasal dilator is U.S. Pat. No. 1,292,083 to Sawyer, which has two pads with metal loops that are attached to the outside of the nasal passages above the nostril on each side of the nose with an adhesive. A resilient member is attached to the pads and exerts a pulling force on them, thereby causing the nasal passage to be dilated. U.S. Pat. No. 1,950,839 to Chirila is similar to the Sawyer patent except that Chirila uses suction cups instead of adhesive pads. In both instances, the resilient member is a single metal spring and the resilient force is determined by the size and spring rate of the resilient member. These designs are difficult to fit and can cause injury to the user if the resilient member should come loose. This would be a significant problem for a user who is asleep and moves, causing the resilient member to become dislodged.

Patents which are part of the second alternative include U.S. Pat. No. 5,546,929 to Muchin and Spanish Patent 289,561 issued to Miguel Angel Aviles Iriarti. Generally speaking, they teach that a single resilient member, or spring, made from a flat piece of plastic extends over the bridge of the nose to the lateral wall and is covered by a pad with adhesive material that extends around the spring member. The spring is inset centrally in the pad, and the pad is located over the nose bridge and adheres to the outside of the nasal passages. This enables the respective ends of the spring to apply a pulling force on the outside of the soft tissue of the nose, thus dilating the nasal passages.

A similar dilator is disclosed in U.S. Pat. No. 5,476,091 to Johnson, except that in the case of the Johnson patent the single plastic resilient member is replaced by two parallel but not connected resilient members that provide the spring force to pull on the nasal valve external wall. The Johnson patent has a top and bottom pad to contain the resilient members which also have notches at each end to reduce delamination forces on the dilator. The dilator of the Johnson patent forms a truss which has a flexible strip material that defines the first and second end regions and an intermediate segment. The first and second resilient bands extend over the length of the truss and generate a force when the end regions are attached to the skin which lifts the underlying tissue upwardly and thereby dilates the nasal passages.

U.S. Pat. No. 5,533,499 to Johnson is a variation of the dilator shown in U.S. Pat. No. 5,476,091. It teaches that two parallel but not connected resilient members are mounted on a single base pad. Each of the end regions of the nasal dilator are adhesively fixed to the external walls of the nasal passages, while the interconnecting truss member passes over the bridge of the nose. The nasal strip configuration of the '499 Johnson patent turned out to be difficult to fabricate and subject to delamination of the resilient members.

U.S. Pat. No. 5,533,503 to Deubek et al is a further development of the nasal dilator disclosed in the two Johnson patents discussed above. Deubek has two parallel but not connected resilient members that are mounted between top and bottom pads. This patent discloses a new pad configuration at each end of the dilator which is designed to improve the ease of manufacture and prevent delamination of the resilient members. The dilator of Deubek also has a truss with pads at each end and an intermediate section that bends over the bridge of the nose. The resilient members generate a force which pulls on the lateral wall, causing the nasal passage to open.

U.S. Pat. No. 5,553,605 to Muchin is related to U.S. Pat. No. 5,546,929 of the same inventor. The '605 patent describes the same nasal dilator design shown in U.S. Pat. No. 5,546,929, except that the nasal dilator is transparent. It also has a single resilient member that crosses over the bridge of the nose and terminates in two pads that attach to the lateral wall on each side of the nose.

The Spanish patent, the two Muchin patents, the two Johnson patents, and the Deubek et al patent all have a single band that crosses the bridge of the nose which contains the resilient member. The Spanish patent and the Muchin patents use a single resilient member, while the Johnson and Deubek et al patents have two parallel but not interconnected resilient members contained in a single truss passing over the bridge of the nose. The spring rate in all these dilators is determined by the design of the resilient member and is set during the manufacture of the nasal dilator.

The present invention teaches about lamination elements resistant to tension, compression and bending forces which can be used as an improved nasal dilator. The lamination element of the present invention works in a manner that is opposite to the manner in which the nasal dilation systems of the Spanish, Muchin, Johnson, and Deubek et al patents work.

SUMMARY OF THE INVENTION

This invention relates to a new field of devices which can utilize lamination elements alone or in combination to stabilize skin, so it can resist deformation caused by external forces. The lamination elements are made up of fabric materials permanently bonded to a thin, resilient layer of plastic which resists tension, compression and bending forces. The lamination element is permanently bonded to a cushion layer located beneath the plastic layer. The lamination element also includes a layer that integrates the outer surface of skin into the lamination element when properly applied by the user. The lamination element uses its resistance to tension, compression and bending to stabilize the skin beneath the center of the lamination element from deflection due to forces acting on the tissue.

The lamination elements are small in size and made up of a top or fabric layer, a plastic layer, a cushion layer, and the skin layer. Each layer of the laminate is bonded to its adjacent layer with a permanent adhesive, with the exception of the bond between the cushion and the skin, which is a strong, but temporary bond. Each level or layer of the laminate can either have the same dimensions or be a different size than the adjacent level. This allows different levels to accomplish different functions, the plastic layer being the most important element of the laminate.

The plastic layer provides the structure that resists tension, compression and bending forces. The plastic layer can be from 0.005 inch to 0.030 inch thick and is typically up to 1.5 inches long. In a preferred embodiment, the width of the plastic layer is between about 0.125 inch to about 0.5 inch; depending on the application. The plastic layer may be solid, may have some porosity, or may have a hole pattern to provide for the ventilation of air and moisture from the skin through the lamination element. The opposite sides of the plastic layer are generally parallel; however, in some cases, the sides may not be parallel, and the plastic layer can have another, e.g. triangular, shape.

Between the plastic layer and the skin is a cushion layer which cushions the skin from the plastic layer. The cushion layer is made from woven polyester or equivalent and provides relief from the rigidity in the plastic layer.

The top of the lamination element is preferably made from woven, stretchable synthetic fabric or the like. The top layer is bonded to the plastic layer and is used to interconnect multiple lamination elements, depending on how they are being applied. The most common interconnection is to connect the lamination elements end-to-end. The stretchable top cover allows the user to adjust the distance between adjacent lamination elements to properly position them on the user's nose.

In a preferred embodiment, the lamination element is used to stabilize the soft tissue forming the lateral wall of the nasal passage to perform the functions of a nasal dilator. In this application, the lamination element is applied so that one of its ends adheres to the skin which covers the cartilage on the side of the bridge of the nose. The other end of the lamination element is positioned on the skin at the cheekbone where the bone provides support for the skin. The center section of the lamination element is pushed against and adheres to the soft tissue of the nasal wall between bridge cartilage and the cheekbone. This resiliently deforms the plastic layer and generates a force that stabilizes the lateral nasal wall, thereby pulling it outwardly and opening the nasal passage. A second and opposite-shaped lamination element is installed on the adjacent lateral wall of the other nasal passage.

Users of the lamination element for stabilizing the lateral wall of the nasal passage will normally use one on each side of the nose. To aid the person in positioning the respective lamination elements, the external fabric layer is preferably extended to connect the two lamination elements end-to-end. This fabric layer is readily deformable, e.g. flexible, acts as a positioner, and can be stretched to assist in properly locating the two lamination elements which stabilize the nasal walls.

The specific elements of the design of the adjustable nasal dilator are shown in the attached drawings and description of the preferred embodiment.

DESCRIPTION OF THE PREFERRED EMBODIMENTS

Figure 1:
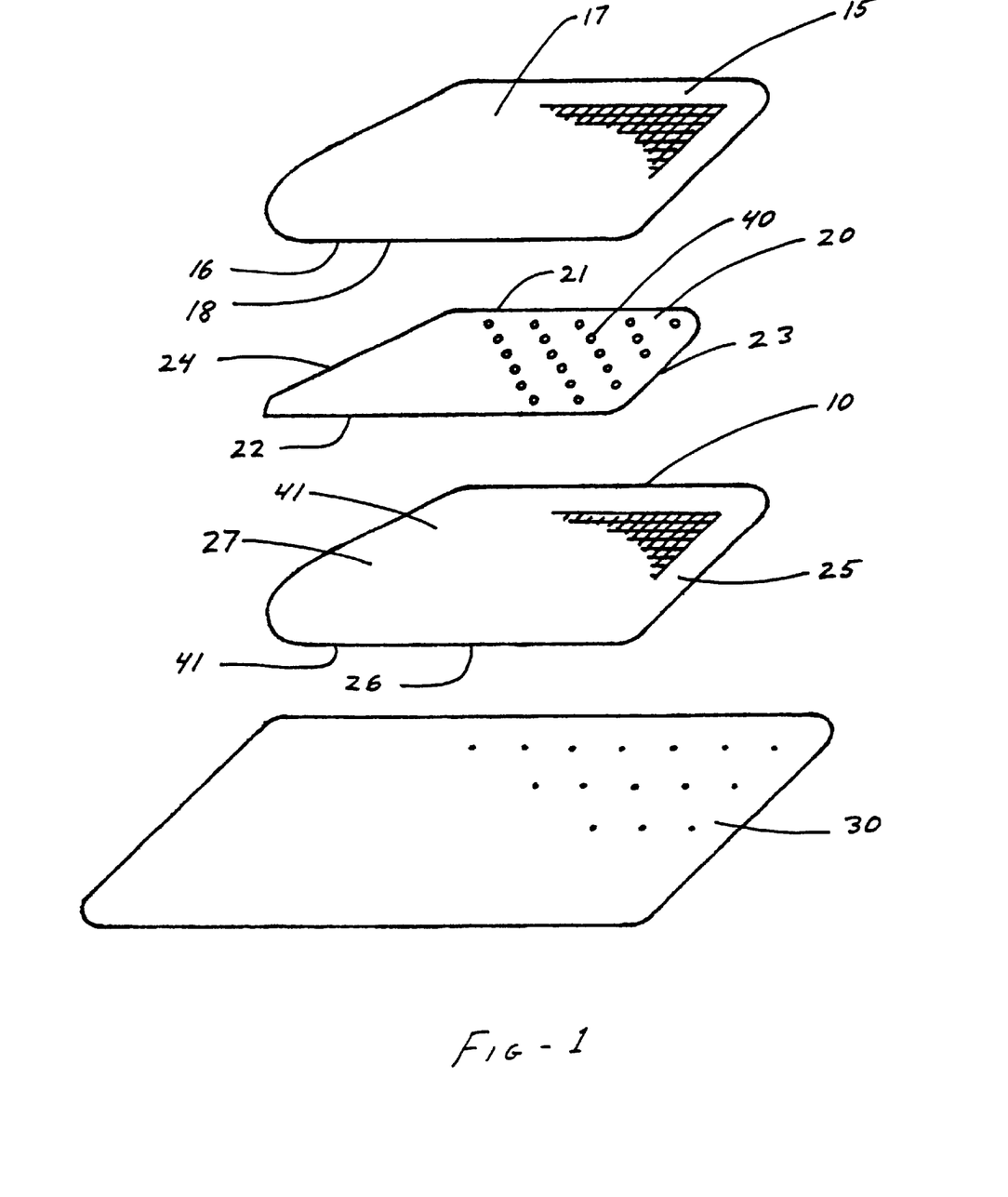
FIG. 1 is an exploded view of a lamination element used as a nasal dilator.

Referring to FIG. 1, a lamination element 10 is made up of a top cover 15 which is bonded to a thin plastic layer 20 which in turn is bonded to a bottom cushion layer 25 that is attached to the user's skin 30 when the skin stabilization system of the present invention is in place. The lamination element 10 stabilizes or strengthens skin with its ability to resist tension, compression and/or bending forces. Top cover 15 of the lamination element 10 is made from a woven polyester or equal and on its bottom side 18 has an adhesive 16 which is a 3 mils acrylic hypoallergenic medical grade pressure sensitive type or equal. The adhesive 16 may or may not cover the entire surface of the top cover 15, depending on the shape of the lamination element 10 and its use. The top cover 15 also has a top surface 17 which can be either the natural color of the fabric material or have a specific color added through dying or printing processes. The top surface 17 can also have printed designs or carry promotional symbols printed on or otherwise applied to it.

A plastic layer 20 is laminated to the bottom surface 18 of the top cover 15. The plastic layer is made from a polyester sheet or equal and will typically vary in thickness from about 0.010 inch to about 0.050 inch. Plastic layer 20 is generally rectangular in shape and typically has a length from about 0.5 inch to about 1.50 inches and a width that can vary from about 10% to about 60% of the length of the plastic layer. The plastic layer has two long edges 21 and 22 which are generally parallel; however, when useful for a given application, long edges 21 and 22 may be angled in relation to each other. Plastic layer 20 has two short edges 23 and 24 which are generally at an angle to each other. When useful, short edges 23 and 24 can be parallel to each other, defining ends which are parallel. Plastic layer 20 can be designed to allow air and moisture to pass through it. This is achieved with perforations 40 that pass through the plastic layer 20 or by making the plastic layer 20 from a plastic material that has a porous structure which allows air and moisture to pass through it. The plastic layer is generally smaller than top cover 15 and is normally recessed from the edge of the top cover. If useful for a given application, plastic layer 20 can have a long edge 21 or a short edge 23 which can be located at the respective edge of the top cover 15. The plastic layer also can be made from transparent plastic for use in a transparent nasal dilator design.

Figure 2:
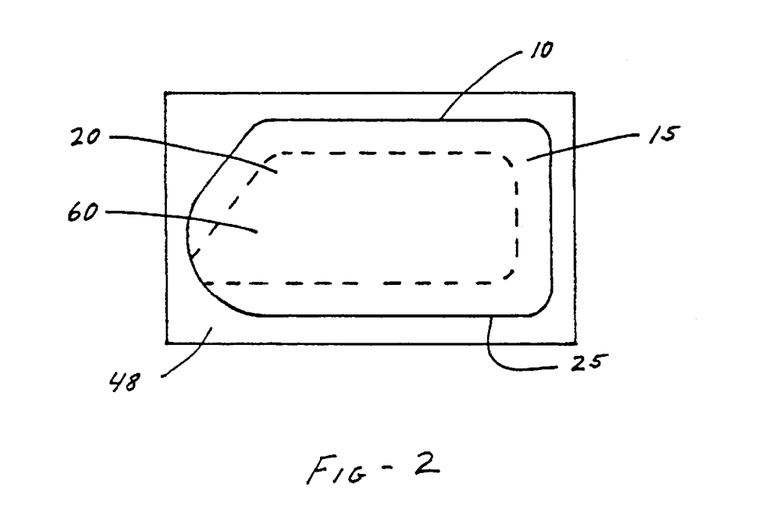
FIG. 2 is a view of a lamination element used as a nasal passage dilator.

Plastic layer 20 and top cover 15 are both laminated to a cushion layer 25. Since plastic layer 20 is normally smaller than top cover 15, the excess surface of the top cover 15 is directly laminated to cushion layer 25. The cushion layer prevents direct contact between the plastic layer 20 and the skin 30. Cushion layer 25 generally has the same shape as top cover 15. The cushion layer is made from a woven polyester or equal and has a bottom surface 26 which carries a 3 mils acrylic hypoallergenic medical grade adhesive 41. Cushion layer 25 has a top surface 27 which has a 1.5 mils acrylic hypoallergenic medical grade adhesive 41 to form a lamination when in contact with bottom surface 22 of plastic layer 20 and bottom layer 18 of top cover 15. The lamination element 10 is fully functional when the cushion layer 25 is adhesively attached and thereby laminated to the user skin 30 by the medical grade adhesive 41 on bottom side 26 of the cushion layer. Depending on the specific use of the lamination element 10, the adhesives on the bottom side 26 or top side 27 of the cushion layer 25 may or may not completely cover the bottom surface 26 or top surface 27, respectively, of the cushion layer. FIG. 2 shows a single lamination element 10 on which a release liner 48 protects the adhesive 41 on bottom side 26 of cushion layer 25 during storage and shipment.

The lamination element 10 makes the user's skin 30 part of the overall lamination to perform its function of stabilizing the user's skin 30 by resisting tension, compression and/or bending forces. The lamination element 10 stabilizes the soft tissue between two or more skin 30 surface areas supported by bone or cartilage, e.g. the wall of the nasal passages.

Figure 3:
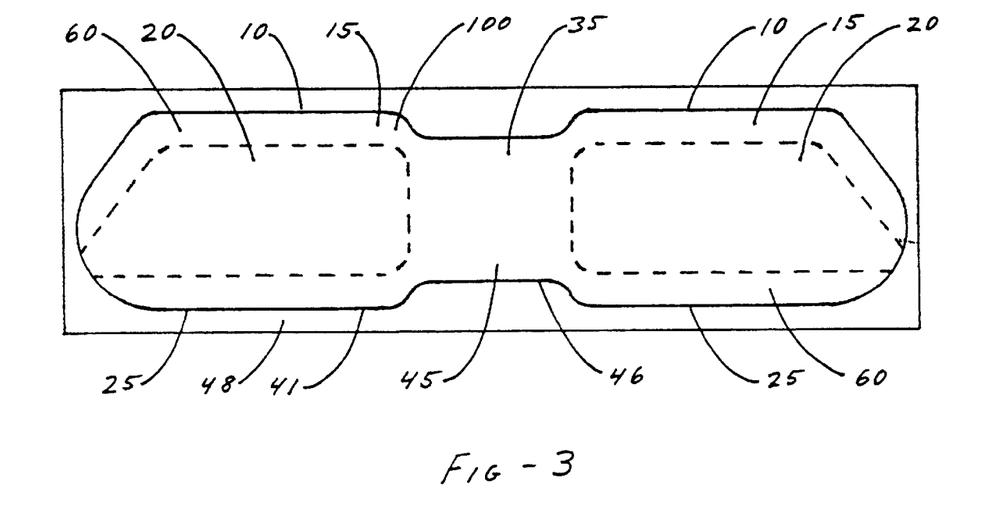
FIG. 3 is a view of two lamination elements linked end-to-end for use as a nasal passage dilator.

FIG. 3 shows two lamination elements 10 which have been joined end-to-end by an end-to-end link 35 consisting of an extension 45 of top cover 15 laminated to an extension 46 of cushion layer 25. The end-to-end link 35 is used to position one lamination element 10 in relation to the second lamination element 10 to assist in properly positioning both ends of the nasal dilator assembly, which is typically made up of more than one, i.e. two, lamination elements 10. The two lamination elements 10 are attached to a release liner 48 which protects the adhesive 41 on the bottom of the cushion layer prior to the application of the lamination elements 10 to the user's skin 30. The release liner 48 is discarded by the user prior to the application of the skin stabilization system.

Figure 4:
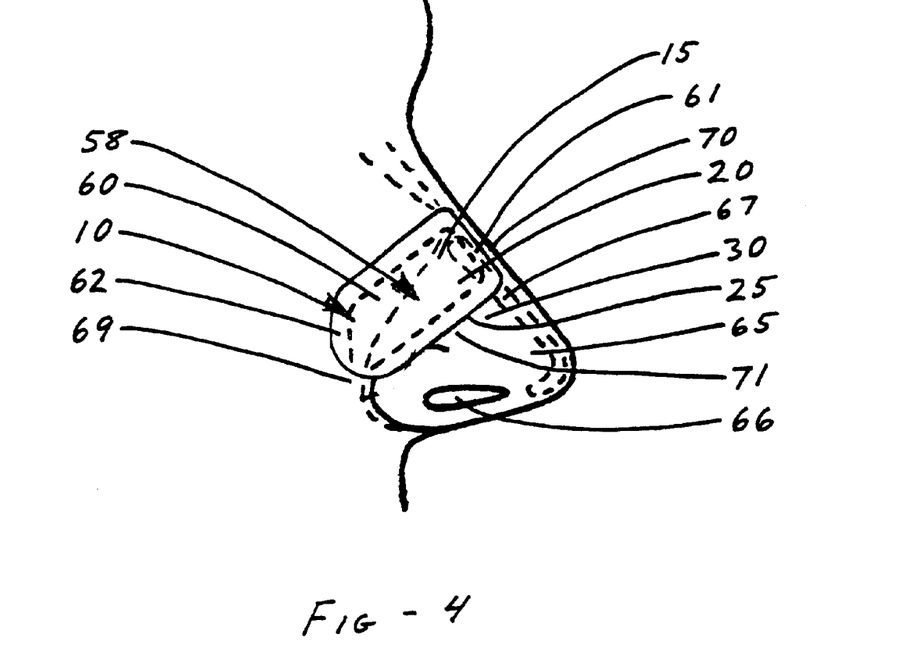
FIG. 4 is a view of a single lamination element located on the user's nose.

FIG. 4 shows a single lamination element 10 in use as a nasal dilator 60. The nasal dilator 60 consists of a top cover 15 laminated to a plastic layer 20 which is laminated to the cushion layer 25 and, when installed, is effectively further laminated to the skin 30 on the side of the nose 65. Top cover 15 and cushion layer 25 of nasal dilator 60 extend beyond the plastic layer 20. A first dilator end 61 is laminated, e.g. adhesively attached, to the user's skin 30, where it is reinforced and supported by cartilage 67 located on the side of a bridge 70 of the user's nose 65. The other, second end 62 of the dilator is laminated to the user's skin 30, where it is reinforced and supported by cheekbone 69 which terminates adjacent to nose 65. With the nasal dilator 60 laminated to portions of the user's skin 30 supported by either bone or cartilage, a center section 58 of the dilator is adhesively attached and thereby laminated to a soft lateral wall 71 of a nostril 66 where the ability of the plastic layer 20 to resist bending stiffens the lateral wall 71, thereby preventing it from being drawn in when the user inhales, thus facilitating the breathing of the user.

Figure 5:
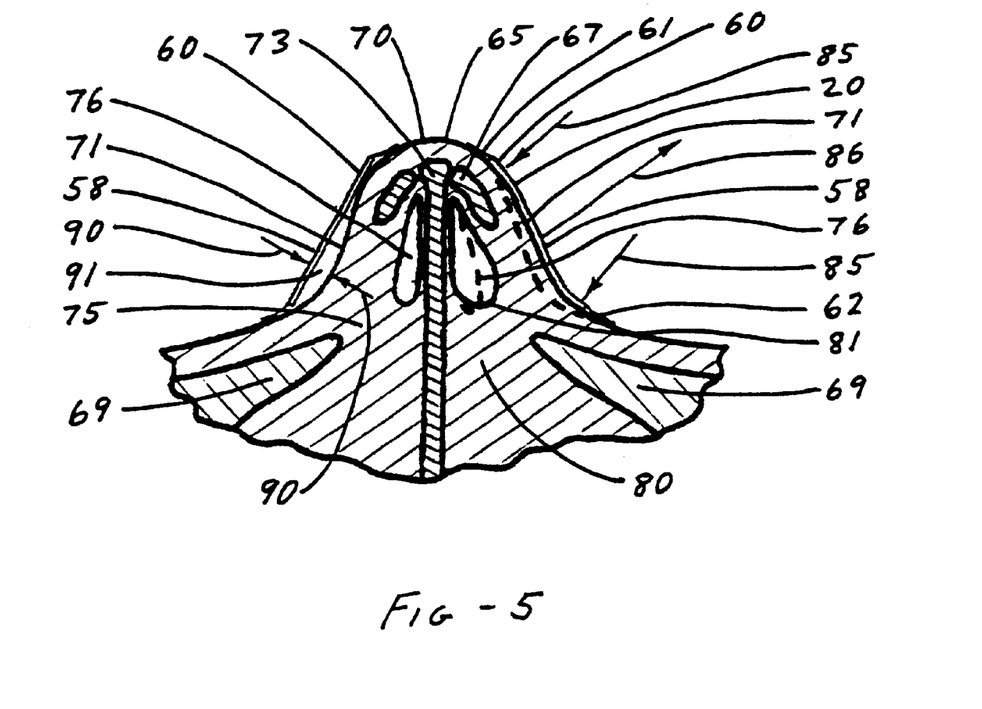
FIG. 5 is a sectional view through FIG. 4 showing the application of the lamination element.

FIG. 5 shows the appearance of nose 65 before the nasal dilator is applied to lateral wall 71 when the nasal passage 76 at the left side 75 of the septum 73 is restricted. The nasal dilator 60 is shown as it is positioned before it is laminated to the lateral wall of the nose. Prior to deflection of the plastic layer 20, there is a gap 91 between center section 58 and the soft lateral nose wall 71. The size of the gap is shown by arrows 90 in FIG. 5. The right side 80 of septum 73 shows the nasal dilator properly laminated to lateral wall 71 of nose 65, thereby eliminating gap 91 and causing the restricted nasal passage 76 (dashed line) to expand outwardly.

The nasal dilator 60 becomes deflected from its relaxed, flat configuration when it is properly applied and positioned to laminate it to the lateral wall of nasal passage 66. The expansion of the nasal passage 81 is due to the force from the resiliently deflected plastic layer 20 of the dilator pulling outwardly on the soft tissue forming lateral wall 71. Force vector arrows 85 and 86 show the direction of force applied to the nose 65 by the nasal dilator 60 when it is installed. At the first and second ends 61, 62, force vector arrows 85 push against the skin and subject it to a compression force. Cartilage 67 and cheekbone 69 support skin 30 against this compression force. In addition, the force urges the first and second ends of the nasal dilator against the skin, thereby preventing an accidental separation of the dilator ends from the skin and maintaining a secure Connection. At the same time, the force vector arrow 86 at the center of the nasal dilator 60 exerts a lifting force on lateral nose wall 71 which causes the lateral wall to move from the dashed line to its new, dilated position shown on the right side 80 in FIG. 5.

FIG. 2 shows a single nasal dilator 60 which can be used on one nostril 66. FIG. 3 shows a nasal strip or dilator 100 which dilates both nasal passages. It is made from two lamination elements 10 that have been joined end-to-end by end-to-end link 35 consisting of an extension 45 of the top cover 15 laminated to an extension 46 of the cushion layer 25. The end-to-end link 35 passes over the bridge 70 of the nose 65 to assist the user in positioning each of the lamination elements 10 that make up dual nasal dilator 100. The end-to-end link 35 made up of the extension 45 of the top cover 15 and the extension 46 of the cushion layer 25 forms an elastic, readily deformable connection between the two lamination elements 10 of dual nasal strip 100. When the dual nasal strip is to be applied to the nose 65, the user can stretch the end-to-end link 35 over the bridge 70 of the nose 65 to properly position each of the lamination elements 10 over their respective lateral walls 71 on each side of the nose 65.

Figure 6:
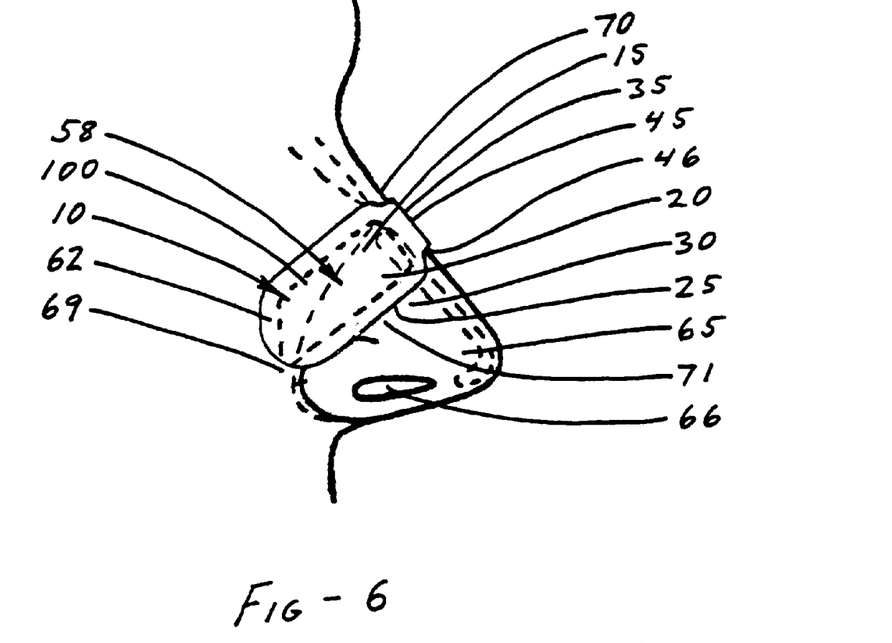
FIG. 6 is a view of two lamination elements linked end-to-end located on the user's nose.
Figure 7:
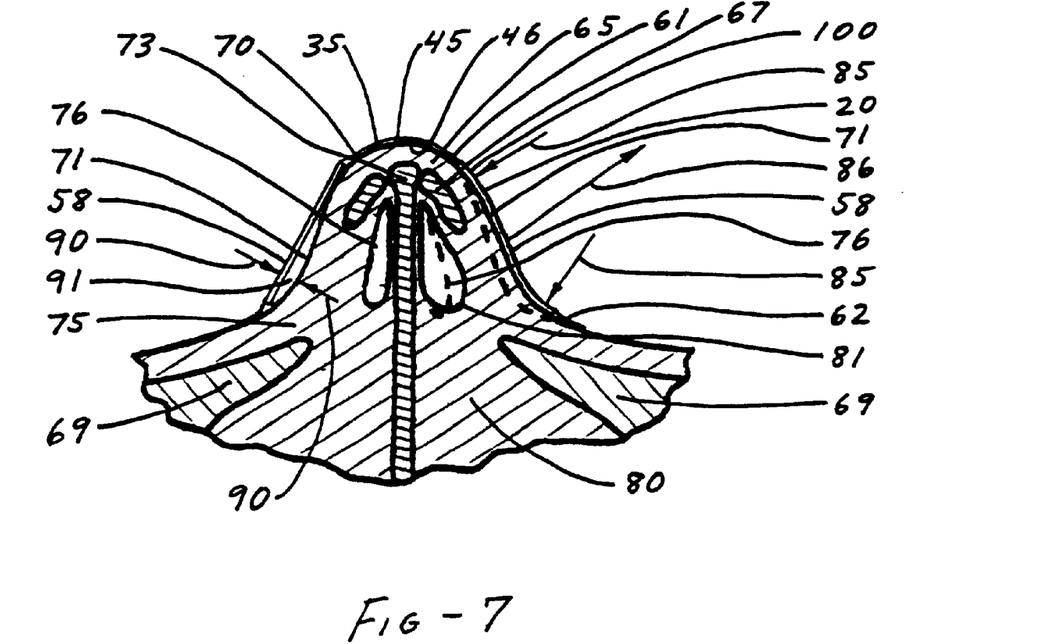
FIG. 7 is a sectional view through FIG. 6 showing the application of two lamination elements.

FIGS. 6 and 7 show how the dual nasal strip 100 is installed on the user's nose 65. On the side 75 of the septum 73, the dual nasal strip 100 is shown as it looks prior to being laminated to the lateral wall 71. The restricted nasal passage 76 shows the reduced area that inhibits breathing. Right side 80 of the septum 73 shows dual nasal strip 100 properly laminated to lateral wall 71 of the nose 65, causing restricted nasal passage 76 (dashed line) to expand to the open nasal passage 81 because the resilient force generated by plastic layer 20 of the nasal strip pulls the soft tissue lateral wall 71 outwardly. The force vectors show the direction of force applied to the nose 65 by one of the two lamination elements 10 which make up the dual nasal strip 100 when it is installed. At the first and second ends 61, 62, the force vectors 85 apply a compression force against skin 30 supported by cartilage 67 and cheekbone 69. At the same time, force vector 86 at the center section of the lamination element 10 applies a lifting force on the lateral nose wall 71 which causes it to move from the dashed line to its dilated position shown on the right side 80 in FIG. 7.

Tests have been performed to establish the dilating forces on the lateral wall 71 of the nose 65. By deflecting 30 the plastic layer 20 by the depth of the gap 91, the resulting lifting force on the lateral wall 71 can be established. The lifting force is represented by the force vector arrow 86 at the center of the lamination element 10. The lifting force results in equal but opposite compression forces which are represented by force vector arrows 85 at the first and second ends 61, 62 of the lamination element. The tested lamination element had a plastic layer 20 made of 0.020 inch thick polyester sheet, a width of 0.4 inch and a chord length (along the centerline of the plastic layer) of 1.050 inches. The results shown are the average results of repeated tests to establish the force levels:

| Lamination Element 10 Deflection 91 | Lifting Force Vector 86 | Compression Force Vector 85 |
|---|---|---|
| .03125 inch | 35.44 grams | 17.72 grams |
| .0625 inch | 81.31 grams | 40.66 grams |
| .09375 inch | 131.17 grams | 65.59 grams |

0.03125 inch 35.44 grams 17.72 grams
0.0625 inch 81.31 grams 40.66 grams
0.09375 inch 131.17 grams 65.59 grams The compression forces are half of the lifting forces on the lateral wall 71 of the nostril 66. This makes the dual nasal strip 100 much more comfortable for the user than nasal strips made according to the prior art. As the lifting force vector 86 is applied and lateral wall 71 expands outwardly in response, the lifting force vector 86 diminishes until an equilibrium is achieved. The dual nasal strip 100 only applies the lifting force vector 86 required to stabilize the lateral wall 71, thereby further contributing to the user comfort.

The dual nasal strip 100 can be fabricated using a transparent top cover 15 and a transparent cushion layer 25 which can be made of a transparent perforated polyethylene or polyurethane. The top cover 15 has hypoallergenic medical acrylic pressure sensitive-type adhesive 16 or equal on the bottom side 18. The cushion layer 25 carries an acrylic hypoallergenic medical grade adhesive 41 on the top surface 27 and the bottom surface 26. At the same time, the plastic layer 20 can also be made from transparent plastic for use in a transparent dual nasal strip 100 design.

The description of the preferred embodiment described herein is not intended to limit the scope of the invention, which is properly set out in the claims.

What is claimed s:

1. A method of stabilizing skin tissue comprising the steps of providing a stabilizer having first and second end portions separated from each other in a longitudinal direction of the stabilizer; positioning the stabilizer over a skin tissue; resiliently deforming the stabilizer so that each of the end portions applies a first force directed towards the skin tissue and a section of the stabilizer intermediate the end portions applies a second force to the skin tissue in a direction away from the skin tissue; and attaching the resiliently deformed stabilizer to the skin tissue.

2. A method according to claim 1 wherein the step of deforming comprises deforming the stabilizer so that a side thereof facing the skin tissue is convexly shaped.

3. A method according to claim 2 wherein the step of attaching comprises positioning the center section over skin tissue comprising a nasal wall.

4. A method according to claim 3 wherein one of the end portions is attached to skin tissue proximate a cheekbone and another one of the end portions is attached to skin tissue proximate nasal cartilage on a side of a nose bridge.

5. A method according to claim 1 including the step of giving the stabilizer a curvature in the longitudinal direction prior to the step of positioning to thereby increase the forces generated by the stabilizer following the step of attaching it to the skin tissue.

6. A method of dilating a nasal passage formed by a nasal wall located between a nose bridge and a cheekbone of a patient, the method comprising
  (a) providing a resiliently deformable sheet having a length so that it extends from a point on the nasal wall that is short of the nose bridge to a point proximate the cheekbone and does not extend over the bridge of the nose,
  (b) placing the strip over the nasal wall so that one end thereof is spaced from the nose bridge,
  (c) pressing the sheet against tissue of the nasal wall so that a side of the sheet contacts the nasal wall and the sheet becomes concavely deformed, and
  (d) adhering the side of the sheet to the tissue to thereby generate first forces at ends of the sheet proximate the nose bridge and the cheekbone which urge the ends against the tissue, and a second force is generated by a section of the sheet intermediate the ends thereof which pulls the nasal wall outwardly to thereby dilate the nasal passage.

7. A method according to claim 6 including providing a second resiliently deformable sheet and applying the second sheet to a second nasal wall of the patient by repeating steps (b)–(d) of claim 6.

8. A method according to claim 7 including flexibly, deformably and nonresiliently interconnecting the sheets with a connector, and placing the connector over the bridge of the nose.

9. A method of dilating a nasal passage defined in part by a flexible nasal wall disposed between a nose bridge and a cheekbone of a patient comprising the steps of providing a resiliently flexible sheet having a length so that one end can be placed over cartilage in the vicinity of the nose bridge without extending over the nose bridge and another end can be placed over the patient's cheekbone, positioning the sheet over the nasal wall so that one end engages tissue overlying the cartilage and the other end engages tissue overlying the cheekbone while forming a gap between a center section of the sheet and tissue which is part of at least a portion of the nasal wall, closing the gap by pushing the center section into engagement with the tissue which is part of the nasal wall and resiliently deforming the sheet to generate forces at the end regions which bias the end regions against the tissue overlying the cartilage and the cheekbone, respectively, and adhering at least the center section to tissue which is part of the nasal wall whereby a reaction force generated by the resiliently deflected sheet pulls the nasal wall outwardly and thereby dilates the nasal passage.

* * * * *

UNITED STATES PATENT AND TRADEMARK OFFICE
CERTIFICATE OF CORRECTION

PATENT NO.    : 6,478,023 B1
DATED         : November 12, 2002
INVENTOR(S)   : Hanford N. Lockwood It is certified that error appears in the above-identified patent and that said Letters Patent is hereby corrected as shown below:

<u>Title page,</u>
Under Item [22], Filed:, add:
-- [30]  Related U.S. Application Data
        Continuation of Provisional Patent Application Serial No. 60/089,111,
        filed June 12, 1998, abandoned. --

Signed and Sealed this

Twenty-third Day of September, 2003

JAMES E. ROGAN
*Director of the United States Patent and Trademark Office*